United States Patent [19]

Borden

[11] E Patent Number: Re. 33,213

[45] Reissued Date of Patent: May 8, 1990

[54] LIGHT SCATTERING PARTICLE DETECTOR FOR WAFER PROCESSING EQUIPMENT

[75] Inventor: Peter Borden, Mountain View, Calif.

[73] Assignee: High Yield Technology, Mountain View, Calif.

[21] Appl. No.: 262,408

[22] Filed: Oct. 25, 1988

Related U.S. Patent Documents

Reissue of:

[64] Patent No.: 4,739,177
Issued: Apr. 19, 1988
Appl. No.: 907,776
Filed: Sep. 16, 1986

U.S. Applications:

[63] Continuation-in-part of Ser. No. 807,901, Dec. 11, 1985, abandoned, which is a continuation of Ser. No. 807,395, Dec. 10, 1985, abandoned.

[51] Int. Cl.[5] ..... G01N 15/06; G01N 15/07; G01N 21/49

[52] U.S. Cl. ..... 250/574; 250/575; 356/338

[58] Field of Search ..... 250/573, 574, 575; 356/336, 337, 338, 339, 340, 341, 342, 343

[56] References Cited

U.S. PATENT DOCUMENTS

| | | | |
|---|---|---|---|
| 3,431,424 | 3/1969 | Allen | 356/337 |
| 3,578,867 | 5/1971 | Barrington | 356/338 |
| 3,622,796 | 11/1971 | Harris | 250/574 |
| 3,704,951 | 12/1972 | Chupp | 250/574 |
| 3,772,525 | 11/1973 | Goodwin | 250/575 |
| 3,994,603 | 11/1976 | Paschedag | 250/575 |
| 4,221,485 | 9/1980 | Schulze | 250/574 |
| 4,299,489 | 11/1981 | Thery et al. | 356/336 |
| 4,473,296 | 9/1984 | Schofner et al. | 356/336 |

FOREIGN PATENT DOCUMENTS

55/038603 of 0000 Japan .

*Primary Examiner*—David C. Nelms
*Assistant Examiner*—William L. Oen
*Attorney, Agent, or Firm*—Alan H. MacPherson; Richard Franklin; Nathan N. Kallman

[57] ABSTRACT

A particle detector includes a laser, a beam shaping lens, and a pair of mirrors which reflect the shaped laser beam back and forth between the mirrors a selected number of times in order to create a sheet of light or light net between the mirrors. The path of the beam is terminated by a beam stop which contains a photodiode to monitor beam intensity and thereby system alignment. Light scattered by a particle falling through the sheet of light is gathered and transmitted to a photodiode. A peak detector provides a measure of the peak intensity of light scattered by such a particle to a microprocessor, which counts the number of particles falling through the light net in a selected time interval. The microprocessor also uses the peak intensity to estimate the size of the particle.

20 Claims, 10 Drawing Sheets

AIRBORNE PARTICLE DETECTOR
(PRIOR ART)

GLASS FILLED PARABOLA, (cm)
FLAT FRONT TABLE I

| | | | | | | | | | | |
|---|---|---|---|---|---|---|---|---|---|---|
| X (cm) = | 1 | 2 | 3 | 4 | 5 | 6 | 7 | 8 | 9 | 10 |
| O°(deg) = | 15 | 18 | 20 | 20 | 20 | 20 | 19 | 18 | 17 | 17 |

15° RAYS

LIGHT SCATTERING PARTICLE DETECTOR FOR WAFER PROCESSING EQUIPMENT

Matter enclosed in heavy brackets [ ] appears in the original patent but forms no part of this reissue specification; matter printed in italics indicates the additions made by reissue.

CROSS-REFERENCE TO COPENDING APPLICATION

This application is *a reissue application for U.S. Pat. No. 4,739,177 which issued on* a continuation in part of [copending] U.S. patent application Ser. No. 807,901, filed Dec. 11, 1985, now abandoned, which is a continuation of the parent application Ser. No. 807,395 filed Dec. 10, 1985 now abandoned.

FIELD OF THE INVENTION

This invention relates to a particle detector and in particular to a particle detector for monitoring airborne particles or particles in a vacuum, or in a fluid environment.

BACKGROUND

As wafer size increases and as device geometry becomes smaller, particulate detection and control becomes ever more important in semiconductor processing. Monitoring of particulate levels is important in processes which take place in an environment of air at atmospheric pressure, for example exposure of photoresist patterns, and for processes which take place in a vacuum chamber, for example deposition of metal films. Particulate contamination can be reduced for processes which take place in an environment of air at atmospheric pressure by the use of so called clean rooms which employ air filtration systems. Even with air filtration systems, however, processing equipment employs moving parts which generate particles and monitoring of particulate levels is therefore desirable for early detection of system breakdowns which produce excessive particulate levels.

One prior art method for detecting airborne particles is shown in FIG. 1. Sampled air (indicated by arrow 5 in FIG. 1) is drawn through narrow transparent tube 6 by a vacuum pump (not shown) attached to end 6a of cylindrical tube 6. Monochromatic light 1 from a laser (not shown) or white light from a lamp (not shown) is focused by lens 2 to form a focused beam 3 which passes through transparent tube 6 at a selected point along the tube. Light scattered from particles in sampled air 5 drawn through tube 6 which passes through beam 3 is detected by detector 7. Alternatively an opening (not shown) in tube 6 and an air sheath may be provided so that the focused beam passes through the opening in the tube. Detector 7 contains a photomultiplier and its construction is well known in the art. The scattering intensity is roughly proportional to particle size. Such systems commonly detect particles having a mean diameter in a range between 0.1 microns and 7.5 microns and in principle even smaller and larger particles can be detected using the above system.

This prior art particle monitoring device has several drawbacks:

(1) It essentially samples air from a point, i.e. the point of the opening of the tube, and does not provide an adequate measure of particulate contamination over a wider spacial region. Often in a semiconductor processing environment, moving parts of various machinery may produce particles that will not be detected by sampling at a particular point. Thus prior art particle monitoring devices do not adequately monitor particles from multiple or distributed sources.

(2) The prior art monitoring system works in air but not in a vacuum chamber since it requires a flow of air to carry the particles.

(3) Particles may stick to the sides of tube 6 and then become airborne again at a later point in time thereby creating a delay effect.

(4) The physical end 6b of the tube must be placed physically close to the point being monitored which may interfere with other portions of the processing system.

SUMMARY OF THE INVENTION

A particle detector is provided which is suitable for detecting particles which are present in either air or in a vacuum. In one embodiment the detector includes a laser and beam shaping lenses which generate a beam whose height is small compared to its width. The beam is reflected back and forth between two mirrors a selected number of times in order to create a light "sheet" or "net" between the two mirrors. The path of the light is terminated by a "beam stop" which monitors the intensity of the beam thereby providing a measure of system alignment. Light scattered from a particle falling through the light net generated between the two mirrors is detected by one or more photodiodes. Signals generated by the photodiodes are amplified and processed by a peak detector. The peaks above a selected threshold value are counted by a microprocessor, which calculates particle flux density.

In one embodiment the beam is chopped and a lens is employed to focus the beam in order to compensate for beam divergence. Projecting members prevent dust from settling on the reflecting surfaces of the mirrors and also prevent light scattered by imperfections in the mirror surface from reaching the photodiodes. In a specific arrangement, the photocells are located so as to provide direct viewing of the light sheet between the two reflecting mirrors thereby enabling the making of a very compact sensor assembly. Since the reflecting mirrors are moved closer together in the compact sensor assembly, a significant improvement in response to the sensed light beam is realized. In another arrangement which is useful for monitoring particles in high temperature environments, such as experienced with hot or corrosive gases or liquids, the sensor assembly includes a narrow, elongated pipe with attached glass windows to provide a small gap between the reflecting mirrors. The glass windows serve to protect the optical system from corrosion and heat. The housing for the sensor assembly is water-cooled to reduce thermal effects.

Two or more particle detectors of this invention may be ganged together to provide detection of particles falling through a large area, for example 8 inches by 8 inches.

BRIEF DESCRIPTION OF THE DRAWINGS

FIG. 2b shows the shape of the beam emerging from the beam expander shown in FIG. 2a;

FIG. 2c shows a partial side view of the particle detector shown in FIG. 2a;

FIG. 3a shows the scattering cross section for a spherical particle into an angular region between $\theta$ and $\theta+5°$;

FIG. 3b shows the angle $\theta$ and $\theta+5°$ employed in FIG. 3a;

FIG. 5b shows the positive envelope of the signal shown in FIG. 5a;

DETAILED DESCRIPTION

Figure 1:
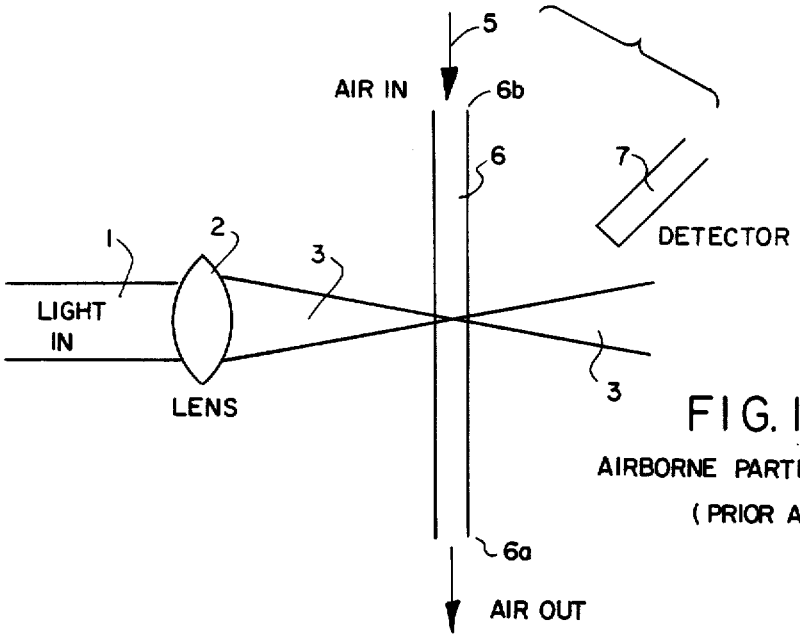
FIG. 1 shows an airborne particle detector of the prior art.
Figure 2B:
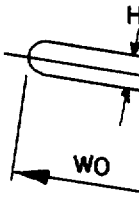
Figure 2A:
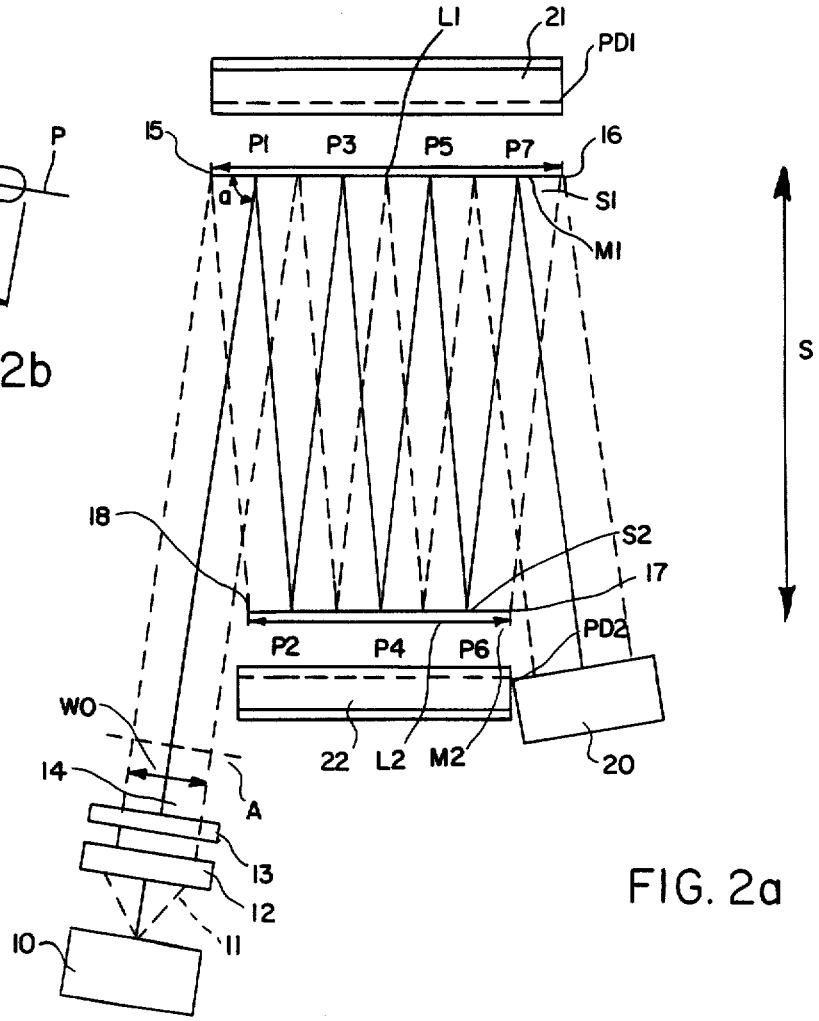
FIG. 2a shows a top view of the particle detector of the present invention.
Figure 2C:
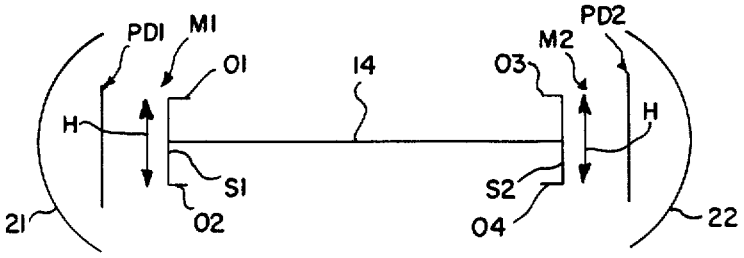

FIG. 2a shows a plan view (not to scale) and FIG. 2c shows a side view of one embodiment of the particle monitor of the present invention. Laser 10 is preferably a semiconductor laser, for example an AlGaAs laser operating at a wavelength of 820 nm. RCA laser No. C86000E and Hitachi laser No. HL8312E are suitable for this purpose. Other sources of light (not necessarily monochromatic) may also be employed with this invention. Beam 11 which emerges from the P-N junction of semiconductor laser 10 is shaped (collimated) by cylindrical beam shaping lenses 12 and 13 which are coupled to shape the beam in the horizontal and vertical planes. Beam 14 which emerges from lens 13 is shown in more detail in FIG. 2b which shows a cross section of laser beam 14 along line A shown in FIG. 2a. In one embodiment, beam 14 is modulated or chopped by circuitry shown schematically in FIG. 4. Beam 14 has an initial height $H_0$ and an initial width $W_0$ determined by the width of the P-N junction (not shown) of semiconductor laser 10 and by shaping lens 12 and 13.

In one embodiment, the width of the P-N junction is approximately 40 microns and beam 14 as it emerges from shaping lens 13 has a width of 2.0 mm and a height of 0.4 mm. Laser 10 and beam shaping lenses 12 and 13 are positioned relative to planar dielectric mirrors $M_1$ and $M_2$ so that the dielectric surfaces $S_1$ and $S_2$ of mirrors $M_1$ and $M_2$ respectively are parallel to each other and perpendicular to the plane P through the center of beam 14 as shown in FIG. 2b. The reflecting surfaces $S_1$ and $S_2$ of mirrors $M_1$ and $M_2$ have a length $L_1$ and $L_2$, respectively, and a height h as indicated by arrows $L_1$ and $L_2$ in FIG. 2a and h in FIG. 2c.

In FIG. 2a the solid line emerging from laser 10 denotes the center of beam 14. Light at the center of beam 14 strikes surface $S_1$ at $P_1$ at an angle of incidence $\alpha<90°$ and is reflected to point $P_2$ on surfaces $S_2$ and in general is reflected back from $P_k$ to $P_{k+l}$ where $k=1, \ldots, 6$ thus creating the zig-zag pattern shown in FIG. 2a. The light reflected from point $P_7$ is received by beam stop 20 which contains a photocell (not shown).

In FIG. 2a the area between each pair of adjacent parallel lines indicated by long dashes represents a segment of light beam 14 traveling towards surface $S_1$ and the area between each pair of adjacent parallel lines indicated by short dashes represents a segment of beam 14 traveling from surface $S_1$ towards surface $S_2$. The separation S between surfaces $S_1$ and $S_2$ and the angle of incidence $\alpha$ are chosen so that the distance between $P_1$ and $P_3$ is the width $W_0$ of beam 14. Since surfaces $S_1$ and $S_2$ are parallel it follows that the distance between $P_k$ and $P_{k+2}$ is $W_0$ for $k=2,3,4,5$. Note that for this selection of parameters S and $\alpha$ the zig-zag path of beam 14 creates a sheet of light that covers the entire area of the trapezoid defined by the end points 15 and 16 of surface $S_1$ and points 17 and 18 of $S_2$. In fact this entire area is covered both by light traveling from surface $S_1$ to surface $S_2$ and by light traveling from surface $S_2$ to surface $S_1$.

Figure 2D:
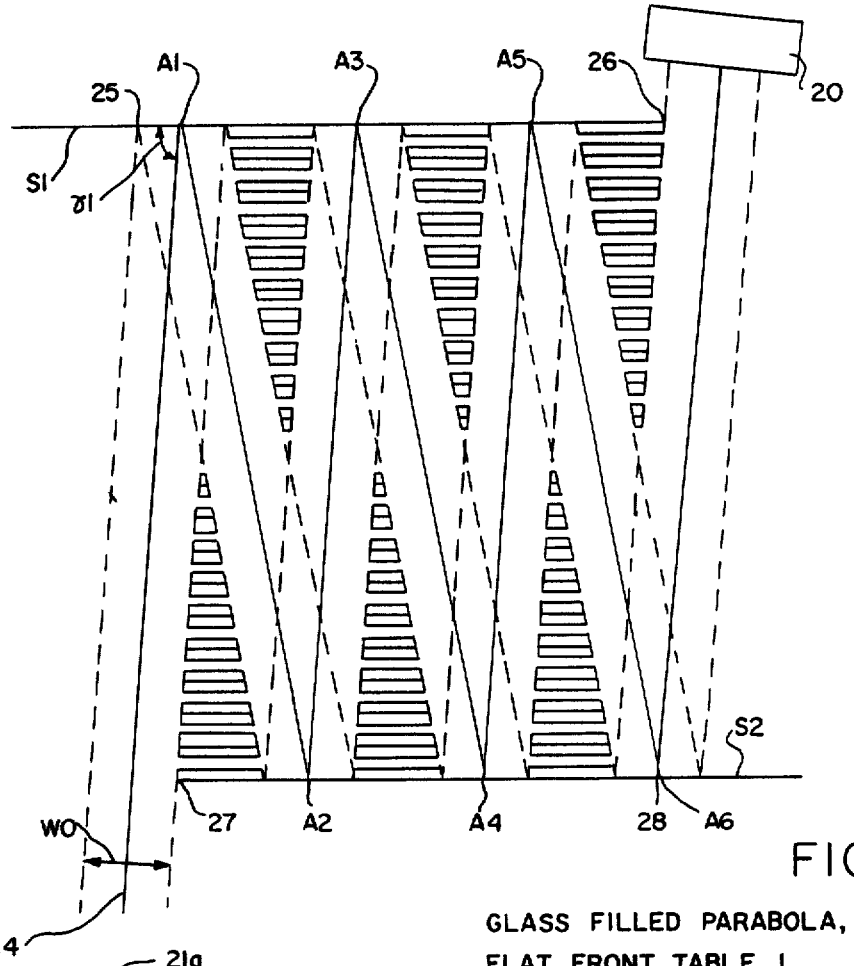
FIG. 2d shows an alternate path for the light employed in the particle detector.

FIG. 2d shows an alternate selection of separation S between surfaces $S_1$ and $S_2$ and an alternate selection of the angle of incidence $\alpha$ wherein the distance between the first and second points $A_1$ and $A_3$ where the center of beam 14 strikes surface $S_1$ is greater than the width $W_0$ of beam 14. For this selection of parameters the zig-zag pattern (light net) created by the reflections of beam 14 does not cover the entire area of the trapezoid defined by points 25, 26, 27 and 28 of reflecting surfaces $S_1$ and $S_2$ respectively. The shaded triangles denote those areas not covered by the beam.

A side view of reflecting surfaces $S_1$ and $S_2$ is shown in FIG. 2c. Collector mirrors 21 and 22 collect light scattered from particles which fall through the light net generated by beam 14 between surfaces $S_1$ and $S_2$. These collector mirrors are typically parabolic in shape and focus the scattered light on photodiodes $PD_1$ and $PD_2$, respectively. The height, h, of mirrors $M_1$ and $M_2$ is small relative to the dimensions of collector mirrors 21 and 22 since mirrors 21 and 22 can only collect light which is reflected out of the plane of the light sheet generated by laser beam 14 and which also "clears" mirrors $M_1$ and $M_2$ and "overhangs" $O_1$, $O_2$, $O_3$ and $O_4$. "Overhangs" $O_1$, $O_2$, $O_3$ and $O_4$ prevent dust from settling on surfaces $S_1$ and $S_2$ and, being opaque, prevent light scattered by imperfections in surface $S_1$ and $S_2$ from reaching collector mirrors 21 and 22.

Note that the side view of the light net created by the reflection of beam 14 from surfaces $S_1$ and $S_2$ is shown schematically as merely a line. Absent compensating measures, the thickness of beam 14 tends to gradually increase as the beam propagates due to beam divergence. This in turn reduces the power density of the beam. This gradual increase in beam thickness is not shown in FIG. 2c for the sake of simplicity.

Similarly, without compensation for divergence, the width of beam 14 also increases with path length but this is not shown in FIGS. 2a and 2d for simplicity. The divergence of the width of beam 14 is generally much smaller than the divergence of the height of the beam since $H_0$ is less than $W_0$.

Dielectric mirrors $M_1$ and $M_2$ are typically made of alternating high and low index coatings on a glass or quartz substrate. An appropriate mirror is a Melles Griot $\lambda/30$ mirror with a proprietary MAX-R coating, such as part number/237, having minimum reflectance of 99.3%. Hence, beam intensity decreases only gradually as the number of reflections of beam 14 between surfaces $S_1$ and $S_2$ increases. Nevertheless, when employing a semiconductor laser with this invention, commercial models of which are currently limited in power, e.g. typically less than 20 milliwatts, surface $S_1$ and $S_2$ are separated by a distance S which is typically larger than $L_1$ and $L_2$ in order to reduce the number of reflections since each reflection reduces the power density of the reflected beam.

It should be noted with respect to both FIG. 2a and FIG. 2d, however, that typically more than the six or seven reflections between surfaces $S_1$ and $S_2$ will be employed but a small number of reflections is shown in the figures for the sake of simplicity. For example, with $S=150$ mm, $W_o=1$ mm, 20 reflections would cover an area approximately 150 mm by 20 mm.

Beam stop 20, which comprises a photocell (not shown in FIG. 2a) in a housing, terminates beam 14 and monitors the power of the laser beam incident on the photocell. This monitoring is accomplished through conventional circuitry (not shown) and serves to indicate when the system components are misaligned. If the laser beam is misaligned, the power of the beam incident on the photocell in beam stop 20 decreases below a preselected level, and conventional circuitry (not shown) causes a signal to be emitted from beam stop 20. This signal may actuate a visual signal device such as a light or may be provided to a microprocessor (not shown).

Figure 2E:
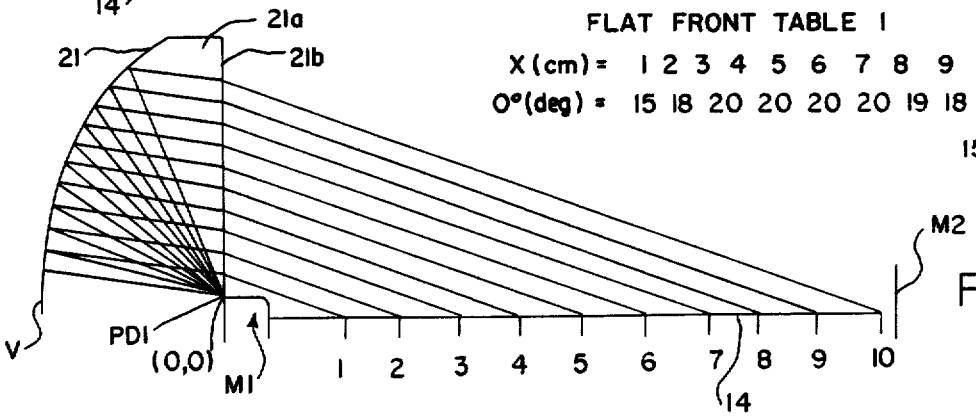
FIG. 2e shows the path of the light scattered along 15° rays reflected by parabolic mirror 21 and focused on photodiode $PD_1$ shown in FIG. 2a and FIG. 2c.

FIG. 2e shows a partial diagram of one embodiment of collector mirror 21 and photodiode $PD_1$. The lower portion of the diagram, which is the mirror image of the top portion, is not shown for the sake of clarity. Mirror 21 is parabolic in shape. The focus of the parabola is 2 cm from the vertex V. The center of photodiode $PD_1$, which is 0.5 cm in width (vertical dimension in FIG. 2e), is located at the origin (O,O) of the coordinate system and is 2.6 cm from vertex V. The distance between mirror $M_1$ and photodiode $PD_1$ is 0.2 cm and mirror $M_1$ is separated from mirror $M_2$ by 10 cm. Region 21a between parabolic mirror 21 and flat surface 21b contains glass having an index of refraction of 1.5 which refracts the rays of scattered light at 15° shown in FIG. 2e toward the horizontal. (Surface 21b is the front surface of the glass). The use of such a glass having an index of refraction greater than 1 increases the angle of acceptance, $\theta_a$, which is the largest angle through which light can be scattered from a particle in beam 14 in front of mirror M1 and still be reflected to photodiode $PD_1$ via lens 21.

Table 1 in FIG. 2e shows the acceptance angle $\theta_a$(in degrees) as a function of x, where x is the distance of a particle in beam 14 in front of mirror $M_1$. As shown in Table 1, the minimum angle of acceptance for particles at least 1 cm in front of mirror $M_1$ is 15 degrees.

Figure 3:
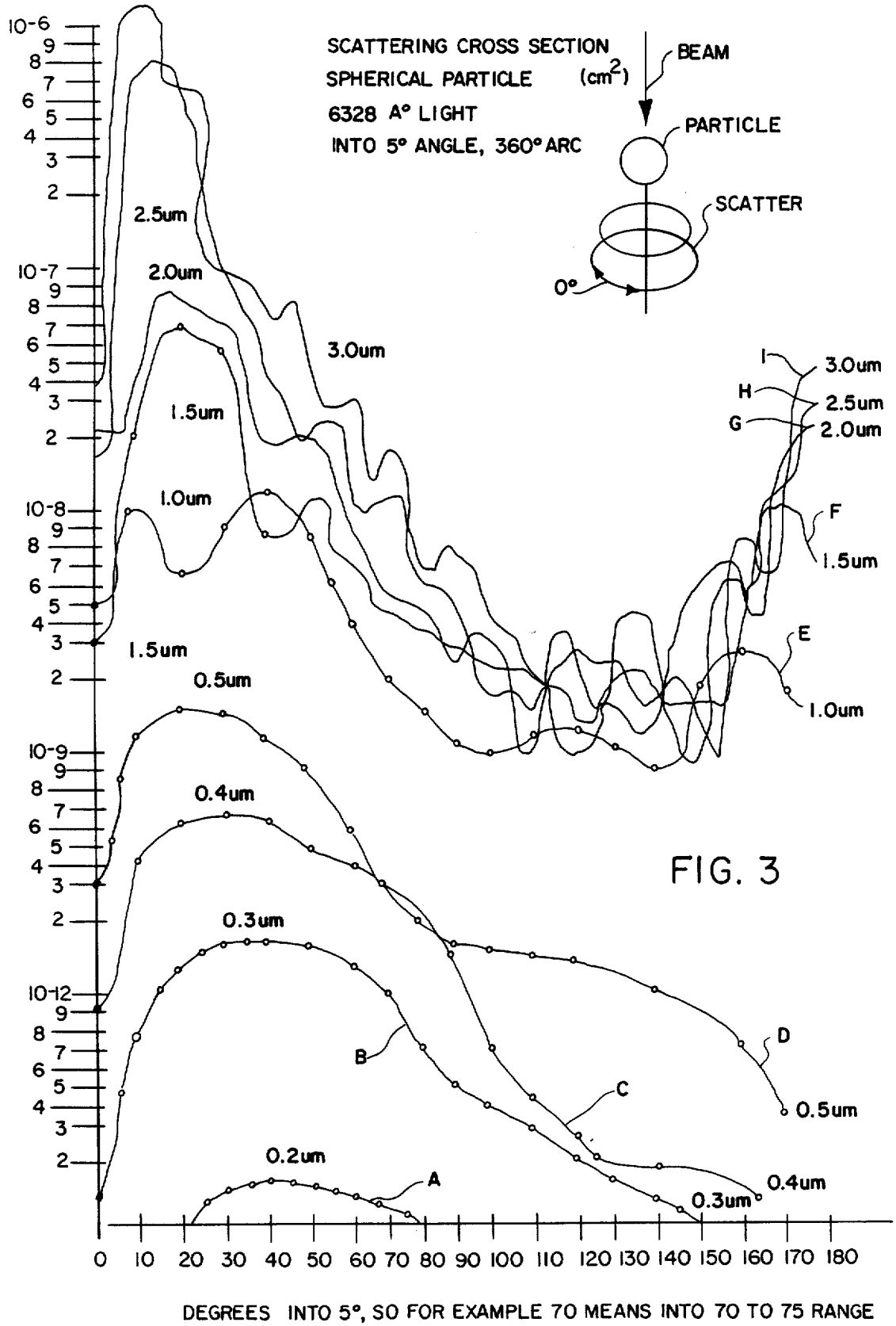

FIG. 3a shows scatter cross-section for spherical particles as a function of angle and particle size for monochromatic light having a wavelength of 6328 Å (from an HeNe laser) incident on the particle.

Figure 3B:
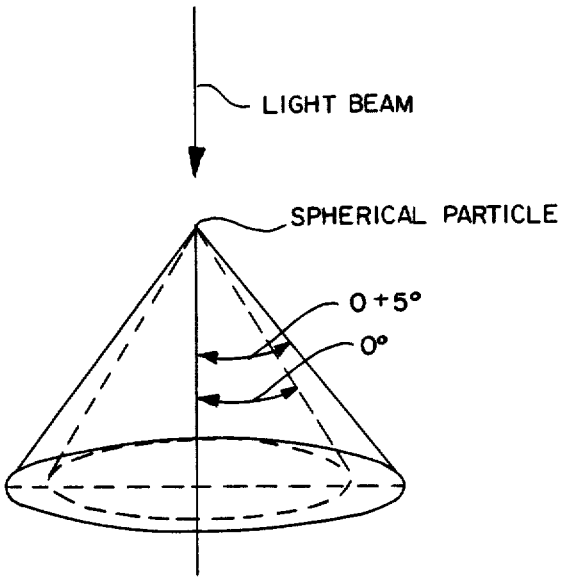

The abscissa in FIG. 3a is labeled in degrees and each abscissa $\theta$ represents the solid region between the right circular cone having angle $\theta$ and the right circular cone having angle $\theta+5°$ as shown in FIG. 3b. The ordinates are measured in $cm^2$.

Curves A, B, C, D, E, F, G, H, and I are scatter cross-section curves for particles having a physical diameter of 0.2 μm, 0.3 μm, 0.4 μm, 0.5 μm, 1.0 μm, 1.5 μm, 2.0 μm, 2.5 μm, and 3.0 μm respectively. Due to interference effects, each particle has an apparatus cross section which is different from its physical cross section. The scattering cross section shown in FIG. 3a is the apparent cross section. An AlGaAs laser diode, as is used in the preferred embodiment, produces light having a wave length of 8200 Å. The intensity of scattered light is somewhat less in this case, but the angular dependence is approximately the same as that shown in Curves A through I in FIG. 3a. Note that the most intense scatter is in the forward direction, for example curve A at approximately 25°. For this reason, the collector lens system shown in FIG. 2c is used with the lenses located approximately perpendicular to the direction of travel of laser beam 14 in order to collect forward scatter. A system with collector lenses located on the sides of the laser net generated by laser beam 14 and generally parallel to the directions of travel of laser beam 14 would be operable but would be much less efficient.

Figure 5A:
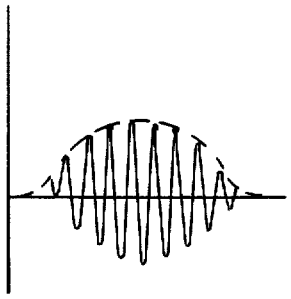
FIG. 5a shows a typical output signal of amplifier 34b shown in FIG. 4.
Figure 5B:
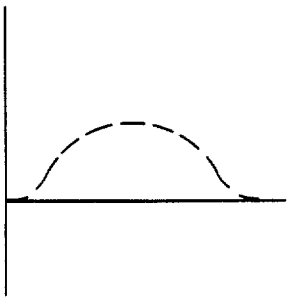

In one embodiment, the light emitted from laser diode 10 is electronically chopped (pulsed) in a conventional way by connecting an AC current source 30 (shown schematically in FIG. 4) to laser diode 10. The output signal of photocell 31 in beam stop 20 (shown in FIG. 2a) is fed back to power source 30 of laser diode 10 in order to maintain a selected constant laser power output. The purpose of chopping the beam is to produce a particle detection system that operates in the presence of daylight or light from other nonmodulated light sources. This greatly improves signal-to-noise ratio since the detector circuit described below looks for signals at the chopping frequency rather than at DC. In one embodiment the frequency of the alternating current source is 3 megahertz and it is preferred to use a frequency sufficiently high so that the laser beam has at least 10 on-cycles during the time it takes a particle to fall under the influence of gravity vertically through the light net generated by beam 14. For example, if it is assumed that a particle falls (under the influence of gravity) vertically downward through a beam having a thickness $H=0.03$ cm at a velocity of 1500 cm/second (which corresponds to a particle falling from rest in a vacuum through a distance of approximately 1.15 meters) then ten cycles must occur in 1/50,000 seconds which corresponds to a frequency of 500 kHz. Since beam 14 is chopped, the scattered light that is received by photodiodes $PD_1$ and $PD_2$ as a particle falls through the light net generated by beam 14 is also chopped. The chopped scattered light sensed by photodiode $PD_1$ is amplified by amplifier 34a. Amplifier 34a is a low noise operational amplifier, for example, amplifier LT1037C made by Linear Technology. Alternately, amplifier 34a can be made of discrete components and a low noise FET, thereby providing an even better signal to noise ratio. It is preferable to mount amplifier 34a within 2 cm of photodiode $PD_1$ in order to minimize noise pick-up in the connections. A second gain stage 34b is mounted in a separate housing indicated schematically by the dotted line in FIG. 4. A typical output signal of amplifier 34b is shown (not to scale) by the solid line in FIG. 5a. The dotted line connecting the positive peaks of the solid line in FIG. 5a is the "positive envelope" of the signal. The output signal of amplifier 34b is sent to mixer 35 which may be, for example, part no. XR-2208, an analog multiplier made by Exar. Mixer 35 also receives the 3 megahertz signal from alternating current source 30. The output of mixer 35 (shown in FIG. 5b) is the positive envelope of the output signal of amplifier 34b. The output signal of mixer 35 is amplified by amplifier 36, for example, part no. LT1055 from Linear Technology, and then provided to peak detector 37 whose output signal represents the peak magnitude of the envelope shown in FIG. 6b as amplified by amplifier 36. The output of peak detector 37 is provided to A/D converter 38 which provides a corresponding digital signal to microprocessor 39.

In this embodiment the output signal of peak detector 37 is multiplexed with the output signal of peak detector 37a. Peak detector 37a is the peak detector associated with photodiode $PD_2$. The remaining circuitry associated with photodiode $PD_2$ is the same as that associated with photodiode $PD_1$ and is not shown in FIG. 4 for the sake of simplicity.

Figure 4:
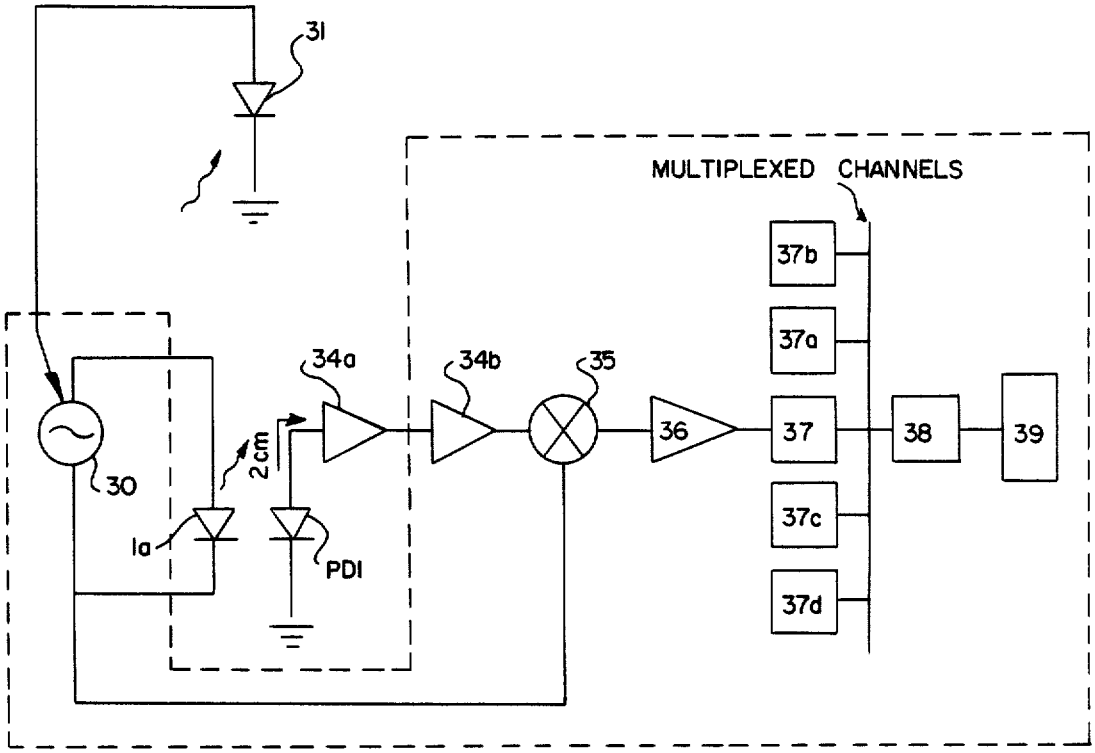
FIG. 4 shows a block diagram of the circuitry used to process the signal received by photodiode $PD_1$.

The peak detectors 37b, 37c, and 37d in FIG. 4 represent peak detectors for photodiodes, not shown, which are used in those embodiments where two or more systems identical to the one shown in FIG. 2a are ganged together, i.e., placed in close physical proximity, in order to provide particle detection for a larger area.

In typical application the computer calculates the particle flux density, that is, the number of particles which pass through beam 14 is a selected time interval. Microprocessor 39 compares the signals it receives from peak detectors 37 and 37a. When both signals are in excess of a preselected threshold value, microprocessor 39 determines that a particle has fallen through the light net generated by beam 14. The peak detectors provide signals which are held for a selected time period, for example, a millisecond, so that only the largest particle that scatters light in a selected time period is counted. This is acceptable in application since most counts are very low, for example in a clean room typically less than one particle per second is counted. The microprocessor keeps this count and tracks the time, thereby enabling it to calculate the particle flux density and to output the result on a display (not shown) or through an interface bus (not shown) to an external computer. The microprocessor can also estimate particle size based on the gain of circuits 34a, 34b, 35, and 36 and the detected signal strength provided by the A/D converter. Typically the output of the microprocessor can also be used to trigger the closing of an interlock relay (not shown) to terminate operation of processing equipment if the detected particle flux exceeds a preset critical level.

In this embodiment of the invention shown in FIG. 2d, particles which fall through the shaded triangles do not, of course, scatter light to collectors 21 and 22. However if it is assumed that the particles which fall through the region bounded by mirrors $S_1$ and $S_2$ and the light beam are uniformly distributed, then one may estimate the total particulate count by multiplying the actual particulate count generated by particles falling through the area actually covered by the zig-zag path of light beam 14 by the total area between surfaces $S_1$ and $S_2$ divided by the area actually covered by the zig-zag path of light beam 14.

Since one principle of operation of this system is the detection of light scattered by a particle falling through the beam, it is critical to maintain an acceptable power density over the entire path of the beam. The power density of the beam, which is defined as the beam power divided by the cross-sectional area of the beam, drops with the distance the beam is propagated due to beam divergence.

Figure 6:
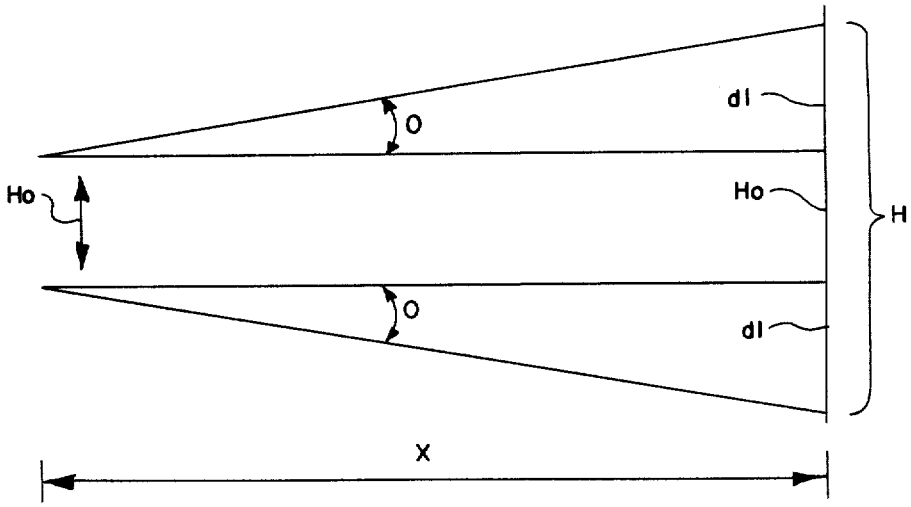
FIG. 6 illustrates beam divergence as a function of path length.

FIG. 6 shows the vertical beam divergence for a collimated beam having an initial height $H_0$ and an initial width $W_0$ (shown in FIG. 2b) as a function of the distance x that the beam has propagated. As shown in FIG. 6, after propagating a distance x the beam thickness H is given by $$H = H_0 + 2d_1 = H_0 + 2x \tan\theta.$$

Moreover, $\theta = \lambda/\pi H_0$ where $\lambda$ is the wavelength of the monochromatic laser beam. Therefore $$H = H_0 + 2x \tan(\lambda/\pi H_0).$$

Since $\theta$ is a small angle $$H = H_0 + 2x\lambda/\pi H_0 = H_0(1 + 2x\ \lambda/\pi H_0^2).$$

A similar analysis shows that the width of the beam after propagating a distance x is given by $$W = W_0(1 + 2x\ \pi H_0^2).$$

Thus, the power density of the beam after the beam propagates a distance x is given by $$P(x) = P_0/HW = P_0/H_0W_0(1 + 2\lambda x/\pi H_0^2)(1 + 2\lambda x/\pi W_0^2).$$

Assuming that $H_0$ is much less than $W_0$, the critical separation (where the power density is approximately one-half the original power density) is given by $$2\lambda x/\pi H_0^2 = 1 \text{ or } x = \pi H_0^2/2\lambda.$$

For example, for $\lambda = 1$ micron and $H_0 = 3 \times 10^{-2}$ cm, the critical separation occurs where $x = 15$ cm.

If the beam is reflected from surfaces $S_1$ and $S_2$ a total of n times the power density becomes $$P(x) = P_0R^n/H_0W_0\,(1 + 2\lambda x/\pi H_0^2)(1 + 2\lambda x/\pi W_0^2)$$

where R is the reflectivity (typically about 99.5% for the dielectric mirror surfaces $S_1$ and $S_2$).

The power of the scattered light received by detector $PD_1$ given by $$P_D = \eta\sigma P(x)$$

where $\eta$ is the detector collection efficiency and $\sigma$ is the particle scattering cross-section, (i.e., the cross-sectional area of the particle perpendicular to the beam). Noise limits the sensitivity of the detector. Noise power is defined by $$P_n = N\,B$$

where N is the Noise Equivalent Power (NEP) of the detector $PD_1$ and B is the band width of the electronic circuit 34a, 34b, 35, and 36. Noise Equivalent Power is a standard measure of the noise power in a frequency bandwidth for a photodiode.

The minimum detectable cross section of a particle is found by equating the power received by the detector to the noise power and solving for $\rho$, the particle scattering cross section, which yields:

$$\rho_{min} = N\,B/\eta P(x) = N\,B\,H_0 W_0(1+\lambda x/\pi H_0^2)(1+\lambda x/\pi W_0^2)/\eta P_0 Rn$$

It is desirable to maximize $\rho_{min}$ as a function of $H_0$. The optimal value of $H_0$ is given by solving $$\partial\rho_{min}/\partial H_0 = 0$$

which yields $$H_0,\ \text{optimal} = \lambda/\pi.$$

Figure 7B:
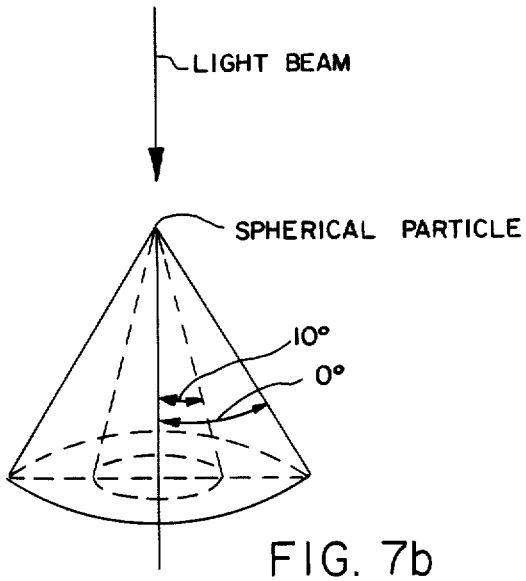
FIG. 7b shows the angular region between a cone having angle 10° and a cone having angle $\phi$.
Figure 7A:
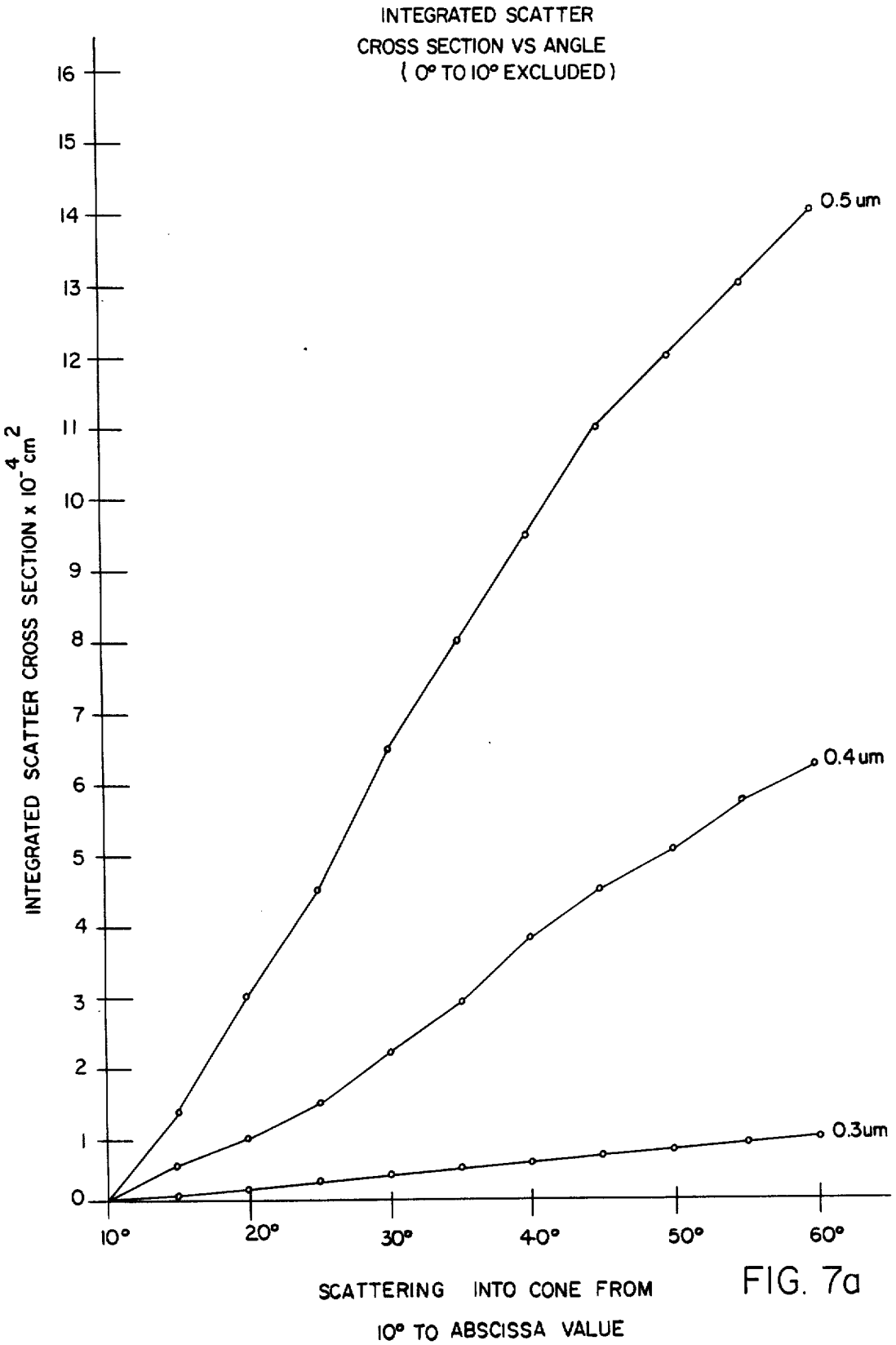
FIG. 7a shows integrated scatter cross section versus angular region.

For example, for a wavelength of 820 nm (AlGaAs laser) and a propagation distance of 50 cm, $H_0$, optimal=0.036 cm. For values of $H_0$=0.036 cm, $W_0$=0.1 cm, B=200 kHz, $N=5\times10^{-13}$ watts/$H_z^{\frac{1}{2}}$, $\eta$=0.5, $P_0$=10 milliwatts, $\lambda$=820 nm, $\rho_{min}=3.7\ 10^{-10}\,cm^2$. For this $\theta_{min}$ a 30-degree detector can easily detect a 0.3 micron-diameter particle. A detector comprising a collector lens 21 and a photodiode $PD_1$ is a thirty degree detector if the photodiode receives rays making an angle up to thirty degrees with the plane of the light net generated by beam 14. FIG. 7 shows the integrated scatter cross section versus angle (0° to 10° excluded) for curves, B, C, and D of FIG. 3a. The abscissa $\theta$ (in degrees) in FIG. 7a represents the region between the right circular cone having an angle of 10° (with the vertical) and the right circular cone having an angle of $\theta$ as shown in FIG. 7b. The power, $P_\theta$, of light scattered into this region is given by $P_\theta = I_o\rho_\theta$ where $I_o$ is the incident power/unit area and $\rho_\theta$ is the integrated scatter cross section corresponding to $\theta$ (FIG. 7a).

As the above analysis shows, the power density decreases with the propagation distance of beam 14 due to divergence.

Figure 8:
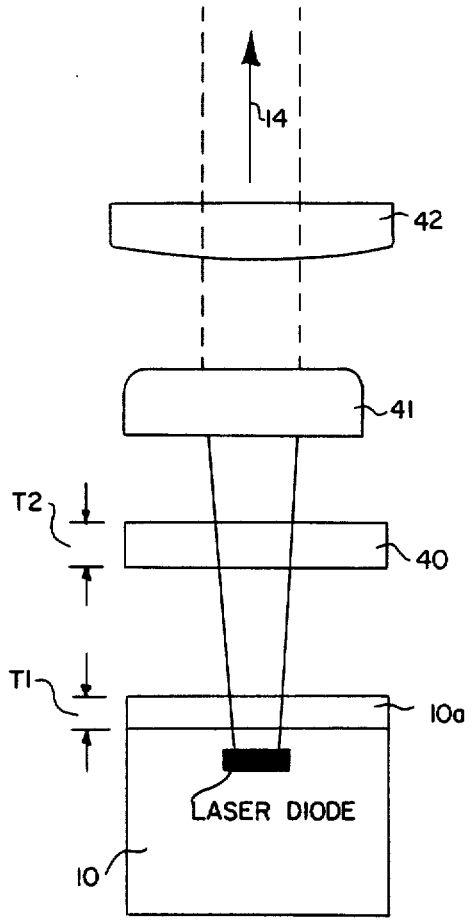
FIG. 8 shows a lens arrangement for compensating for beam divergence.

Beam divergence can be compensated for by, instead of collimating the beam using lenses 12 and 13 as explained above, bringing the beam to a focus that exactly compensates for the divergence angle $\theta$ shown in FIG. 6. This is a technique that is well known in the art, and is discussed, for example, in Melles Griot Optics Guide 3, page 349, 1985. FIG. 8 shows in more detail one preferred embodiment for compensating for this divergence. Laser diode 10 is typically packaged so that light emerging from the p/n junction of laser 10 passes through glass 10a. The thickness $T_1$ of glass 10a affects (by refraction) the dimensions of the beam which emerges from glass 10a and may vary from manufacturer to manufacturer. The focusing qualities of lenses 41 and 42 are selected based on a beam which has passed through a selected thickness T of glass greater than the varying thicknesses for plate 10a typically employed by different manufacturers. Thus, by inserting glass plate 40 having thickness $T_2$ where $T_2$ is selected so that $T_1+T_2=T$, the remainder of the optical system may remain unchanged when different laser diodes employing different glass thickness $T_1$ are used from time to time.

The beam which emerges from glass plate 40 passes through cylindrical lens 41 which focuses the beam in the vertical dimension indicated by the arrow Ho in FIG. 2b. The radius of curvature of lens 40 is selected to exactly compensate for the vertical beam divergence angle $\theta$ shown in FIG. 6. The beam emerging from cylindrical lens 41 then passes through cylindrical lens 42 which has a radius of curvature selected to exactly compensate for horizontal beam divergence (divergence in the width of the beam). Beam 14 emerging from lens 42 thus maintains a constant thickness and a constant width as it propagates between mirrors $M_1$ and $M_2$.

Alternatively, divergence in the thickness H of beam 14 can be corrected by slightly curving the mirror surfaces $S_1$ and $S_2$. The use of cylindrical lenses 41 and 42 described above is preferable to this second method since curved mirrors are expensive and difficult to implement.

Figure 9:
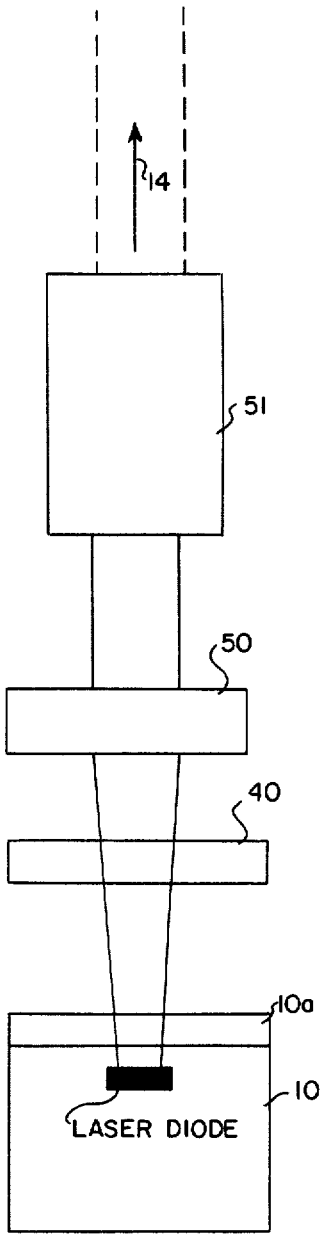
FIG. 9 shows an alternate arrangement for compensating for beam divergence.
Figure 10:
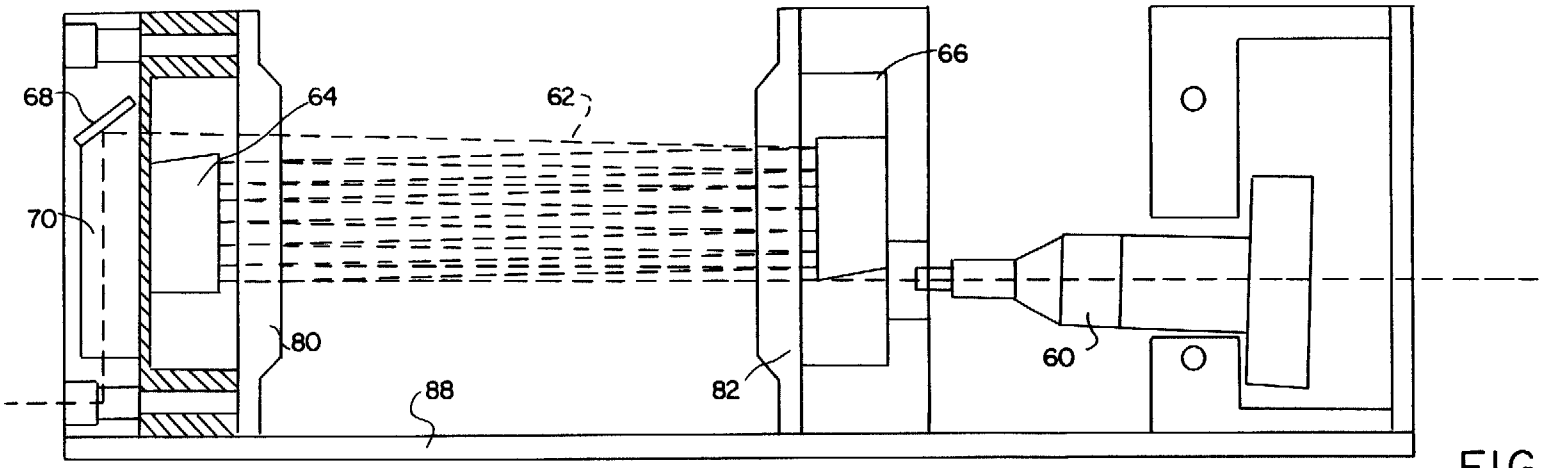
FIG. 10 is a top view of a compact direct view sensor assembly, that is an alternative embodiment of this invention.

A third method of collimation and divergence correction is to use a gradient index lens. Gradient index lenses are available from Melles Griot in the 06LGT product line in consumer specified legnth. A gradient index lens is a glass rod with an index of refraction that varies with diameter. A focusing action results as light propagates through the rod. The focal length of the gradient index lens is determined by the length of the glass rod. FIG. 9 shows one embodiment of the optical means used to compensate for beam divergence employing a gradient index lens. The elements in FIG. 9 that are the same as in FIG. 8 bear the same numerical labels. In FIG. 9, the beam emerging from flat glass plate 40 is received by cylindrical lens 50 selected so that the beam emerging from lens 50 has a desired ratio of height to width. The beam from lens 50 is received by gradient index lens 51 which collimates the beam along the horizontal (width) axis and compensates for beam divergence angle $\theta$ (FIG. 6) along the vertical thickness axis, so that the light net generated by beam 14 has constant thickness.

With reference to FIGS. 10, 11, 12a and 12b, a compact direct view sensor is illustrated. The direct view sensor assembly includes a light source 60, such as a laser cartridge, having lenses that provide a collimated laser beam 62. The beam is directed to a first reflecting mirror 64 at an angle of about 15° relative to the planar face of the mirror 64. The beam is reflected to a second mirror 66 that has a face substantially parallel to that of the first mirror 64 so that a light sheet or light net is produced in the narrow gap between the mirrors. The reflected beam passes over the first mirror 64 to impinge on a photodiode 68. The photodiode indicates the intensity of the light beam that is received to ensure that the laser beam and the optical system of the sensor assembly are operating properly. The beam is reflected from the photodiode into a beam stop cavity 70 which prevents stray light from returning to the optical system, and provides a safety feature.

Figure 11:
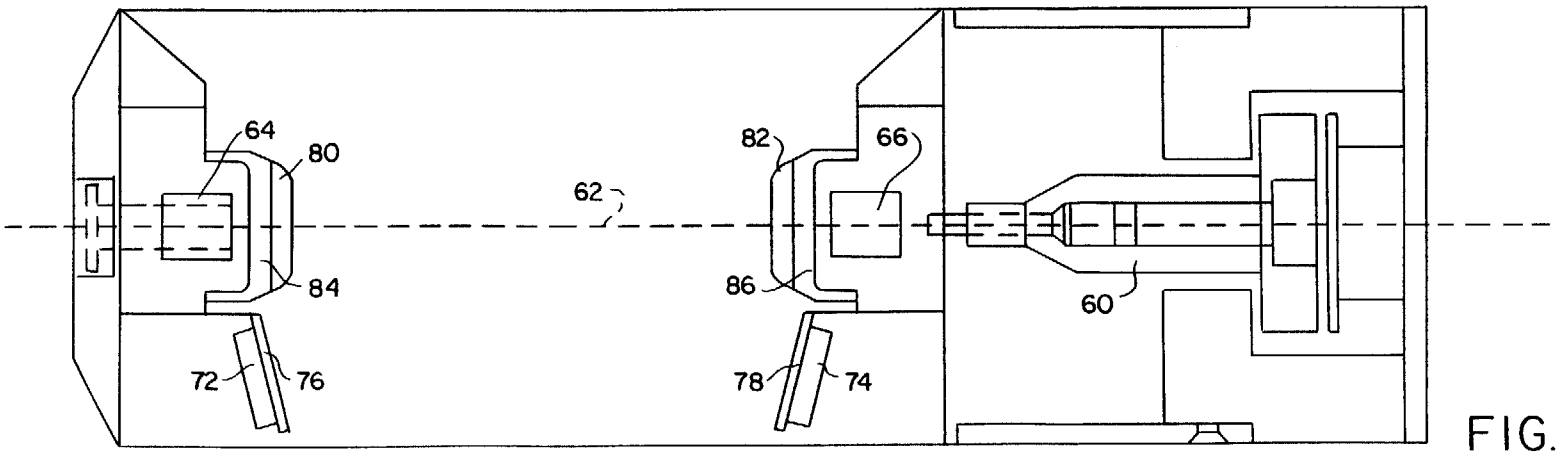
FIG. 11 is a side view of the sensor assembly of FIG. 10.

As illustrated in FIG. 11, photocells 72 and 74 are positioned close to the mirrors 64 and 66 to detect the traversal of particles through the light sheet. The photocells generate signals representative of the incidence of particles passing in the gap between the mirrors. The signals are amplified, peak detected and processed by a microprocessor that computes the particle flux density, as described previously. A visual display is obtained by means of a display monitor that is coupled to the microprocessor. Glass filters 74 and 76 are provided with the photocells to block spurious light of different wavelengths than that of the laser beam. The mirrors have front pieces 80 and 82 which are made with dielectric stacks, formed of a substrate with a MAX-R (trademark of Melles Griot) coating that passes a wavelength of about 780 nanometers. The front pieces are attached to cover glasses 84 and 86 that are seated over the faces of the respective mirrors.

Figure 12:
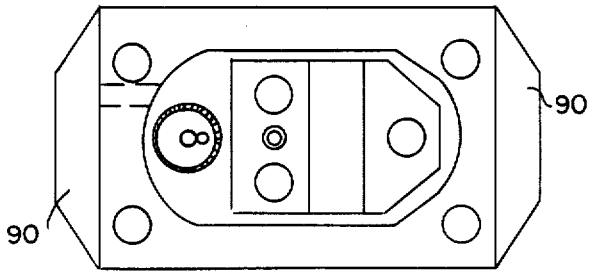
FIG. 12 is an end view of the sensor assembly illustrated in FIG. 11.

The sensor assembly is positioned in a frame 88, and support brackets 90, one being illustrated in FIG. 12, enclose the ends of the frame to form a housing or enclosure for the sensor assembly.

Figure 13:
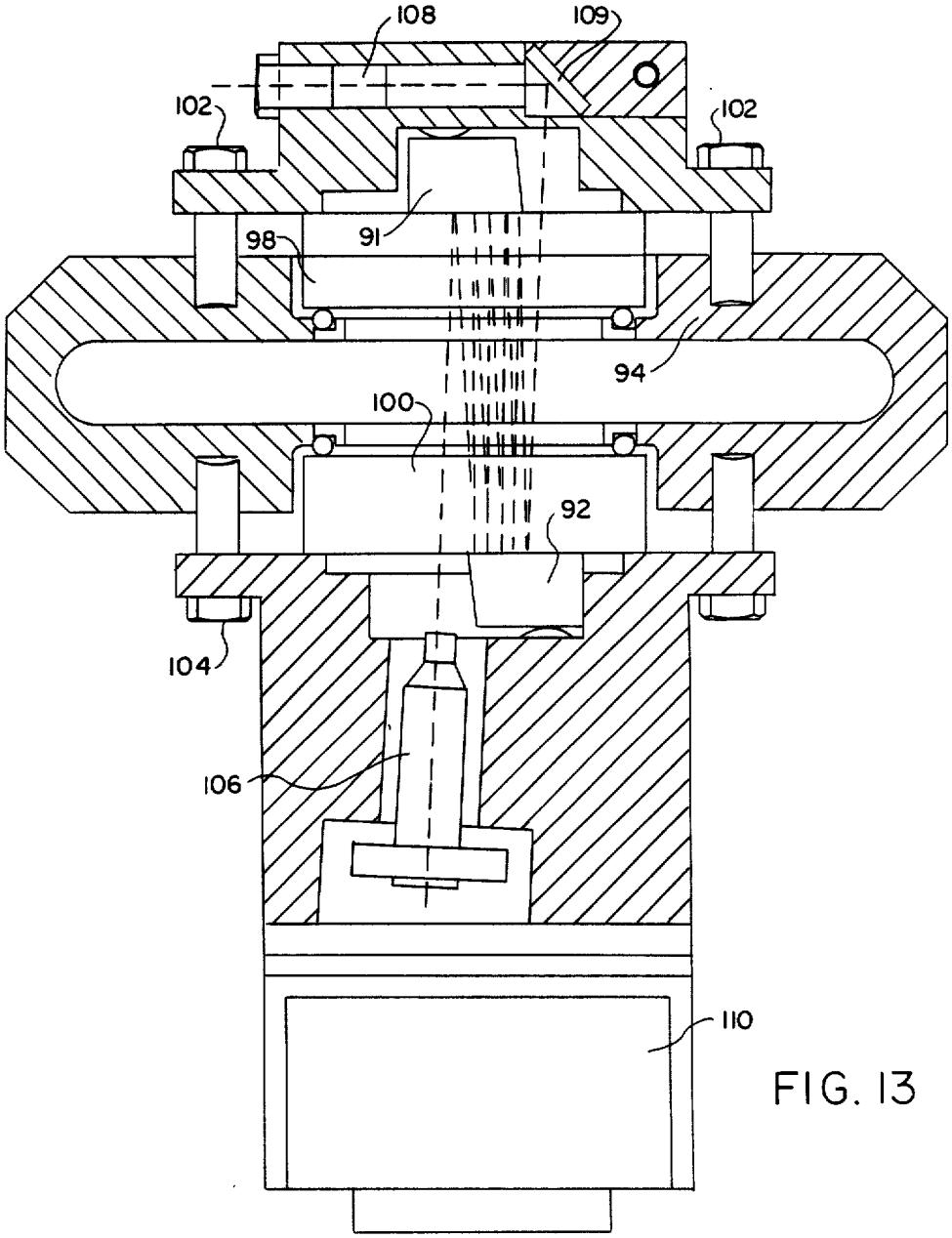
FIG. 13 is a top view of another alternative embodiment of the invention employing a compact sensor assembly including a pipe structure.
Figure 14:
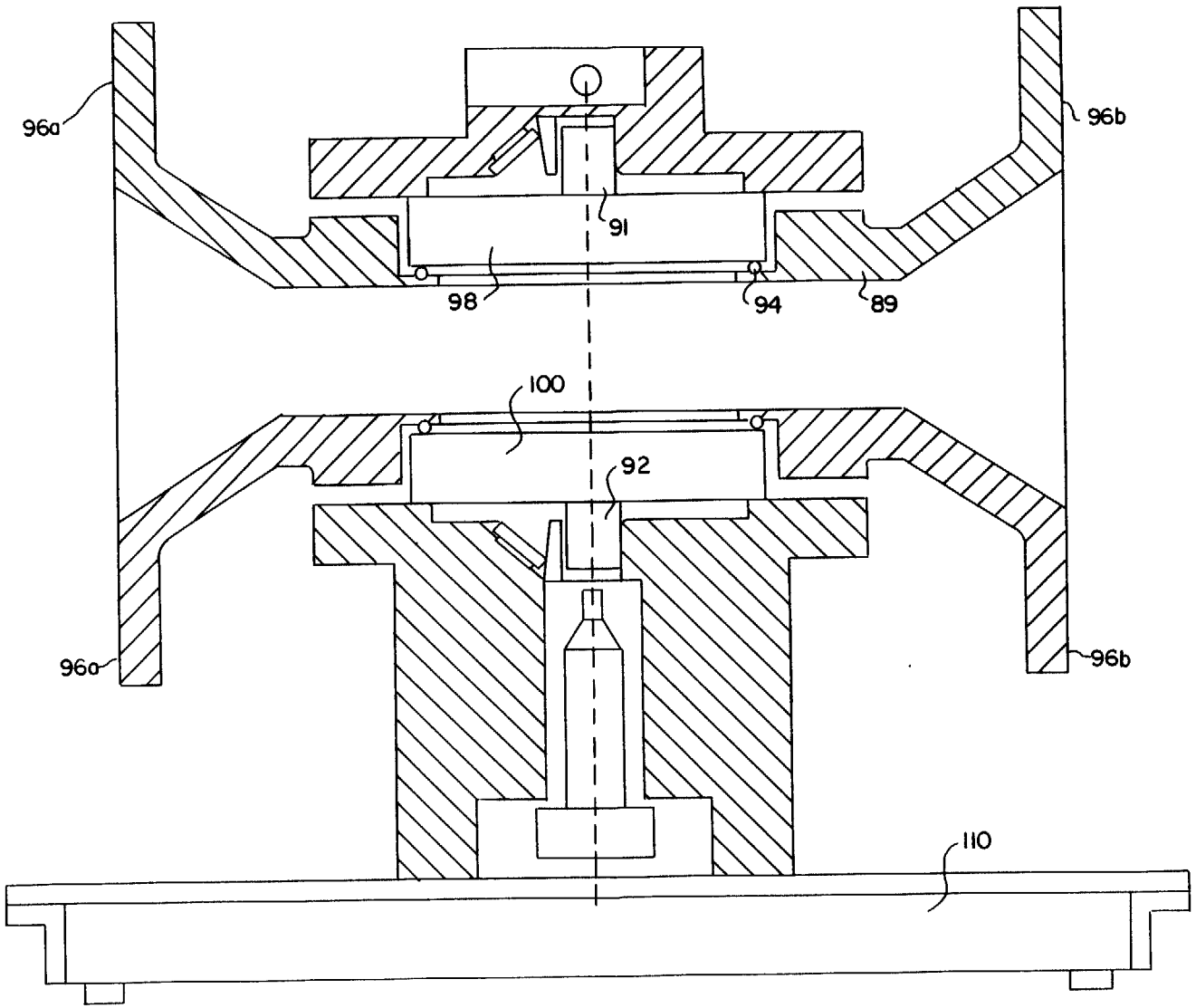
FIG. 14 is a side view of the sensor assembly of FIG. 13.

An alternative embodiment of a sensor assembly is depicted in FIGS. 13 and 14. The sensor assembly, which is useful for particle detection of hot or corrosive gasses or fluids, is made with a pipe section 89 that is disposed in a substantially transverse direction between two reflecting mirrors 91 and 92. The pipe section 89 has a narrow central portion 94 and flared flange portions 96a, 96b which enable coupling the pipe section to standard diameter pipes through which the gas or fluid under detection is passed. Glass windows 98 and 100 are provided between the mirrors and the central cavity of the pipe section. The glass windows protect the optical system from corrosion and heat. The windows are made of a heat resistant, low temperature coefficient glass, such as fused silica. The glass is polished flat on the front and back surfaces. The mirrors are assembled to the windows, which are mounted onto the pipe using fluorocarbon O-rings that are able to withstand temperatures up to 200° C. The mirrors are aligned by tightening two sets of three bolts 102 and 104 that clamp the windows to the pipe, while the O-rings provide the desired play.

When operating in high temperature environments, the housing for the laser 106 and the beam stop structure 108, which includes the photodiode 109, are cooled by circulating cooling fluid or water through channels or pipes positioned in the housing. As previously described, a preamplifier 110 is provided to amplify the intensity of the laser beam.

With the small gap between the mirrors, as embodied in the alternative implementations of FIGS. 10–14, a compact structure that provides improved signal resolution is made possible. The compact structures are made with a reduced number of parts and are less costly to manufacture.

The scope of the invention is not limited to the specific arrangements, materials and parameters disclosed herein. For example, more than two mirrors may be used to generate the light net, and the optical system may be modified to provide a desired path for the light beam. Also, the pipe section described with reference to FIGS. 13 and 14 may be cylindrical, a rectangular channel, or any configuration affording the compact narrow gap between the reflecting mirrors.

I claim:

1. Apparatus for detecting particles in a vacuum, or air or fluid environment comprising:

means for providing a light beam having a defined access;

lens means for shaping said light beam to provide a collimated beam having a predetermined width and height;

first mirror means having a first surface for *reflecting said light beam* [providing multiple reflections of said light beam, the angle of incidence of each of said reflections of said light beam being less than 90°];

second mirror means having a second surface for *reflecting said light beam* [providing multiple reflections of said light beam that is reflected from said first surface, the angle of incidence of each of said reflections of said second surface being less than 90°];

said first and second surfaces of said first and second mirror means respectively being substantially parallel and spaced from each other so that *said light beam is reflected from said first surface to said second surface a first multiplicity of times and from said second surface to said first surface a second multiplicity of times, said light beam having an angle of incidence on said first surface and on said second surface of less than ninety degrees (90°) prior to each reflection from said first surface and said second surface, said first and said second surfaces and said means for providing a light beam being arranged so that* the distance between adjacent points of reflection on each surface is substantially the dimension of the width of said light beam, *said first and second mirror means having highly reflecting surfaces;* photodiode means *including first and second photodiodes* for detecting light that is scattered by particles that traverse said beam, said *first and second* photodiodes being spaced at a distance from each other greater than the distance between said first and second [reflecting] surfaces *of said first and second mirror means.*

2. A particle detector as in claim 1, wherein said first mirror means and said second mirror means comprise planar dielectric mirrors.

3. A particle detector as in claim 1, wherein said angles of incidence are less than or about 15°.

4. A particle detector as in claim 1 further comprising a beam stop for terminating said beam after said beam has been reflected a plurality of times.

5. A particle detector as in claim 4 wherein said beam stop includes means for sensing the intensity of light incident on said beam stop.

6. A particle detector as in claim 5 wherein said beam stop further includes means for emitting a signal when the intensity of light incident on said beam stop falls below a preselected value.

7. A particle detector as in claim 1 wherein said means for providing a beam of light comprises a laser.

8. A particle detector as in claim 1 wherein said first *mirror* means [for reflecting said beam of light] and said second *mirror* means [for reflecting said beam of light] each comprises a mirror curved to reduce the divergence of said beam of light.

9. A particle detector as in claim 1 wherein said lens means includes a lens [having a focal length selected to compensate for beam divergence] positioned between a source of said beam of light and said first *mirror* means [for reflecting], *said lens having a focal length selected to compensate for beam divergence.*

10. A particle detector as in claim 1 further comprising at least one member extending outward from *at least* one of said *first and second mirror means* [mirrors] to prevent dust from settling on *at least one of* said *first and second surfaces, respectively* [surface of said one of said mirrors].

11. A particle detector as in claim 1 further comprising at least one opaque member extending outward from *at least* one of said *first and second mirror means* [mirrors] to prevent light scattered from imperfections in *at least one of* said *respective first and second surfaces* [surface] of said *at least* one of said *first and second mirror means* [mirrors] from being detected by said photodiode *means.*

12. A particle detector as in claim 1 wherein said lens means comprises one or more lenses which produce a beam of light having a height less than its width.

13. A particle detector as in claim 1 further including means for chopping said light beam.

14. A particle detector as in claim 1 wherein said photodiode means for detecting scattered light comprises a collecting mirror, said collecting mirror focusing said scattered light on *one of* said *first and second photodiodes* [photodiode means].

15. A particle detector as in claim 14 wherein said *photodiode* means for detecting further includes means for *providing* [sensing] a *signal* representative of [the] *a* peak amplitude of a light signal received by said *one of said first and second photodiodes* [photodiode].

16. A particle detector as in claim 15 wherein said *photodiode* means for detecting further includes an analog-to-digital converter and a microprocessor, said analog-to-digital converter providing said microprocessor with [the] *a* digital representation of said *signal* representative of said peak amplitude of said light signal received by said photodiode *means.*

17. A particle detector as in claim 1 wherein said lens means comprises a gradient index lens.

18. A particle detector as in claim 1, including a pipe section having a narrow cavity extending substantially transversely to said beam of light.

19. A particle detector as in claim 18, including window means *for protecting said first and second surfaces while allowing said light beam to pass through said window means, said window means being* disposed adjacent to said pipe section and between said first surface and said second surface.

20. A particle detector as in claim 18, wherein said pipe section comprises flanged portions for coupling to external pipes so that fluids or gases can be passed through said narrow cavity.

* * * * *